United States Patent [19]

Filbey et al.

[11] Patent Number: 4,514,577

[45] Date of Patent: Apr. 30, 1985

[54] CHEMICAL PROCESS FOR PREPARING DI-ORTHO BENZYL PHENOLS

[75] Inventors: Allen H. Filbey; Henry G. Braxton, Jr., both of Baton Rouge, La.; Bernard R. Meltsner, Royal Oak, Mich.

[73] Assignee: Ethyl Corporation, Richmond, Va.

[21] Appl. No.: 434,827

[22] Filed: Oct. 15, 1982

[51] Int. Cl.³ .................. C07C 39/14; C07C 37/16
[52] U.S. Cl. .................... 568/744; 568/716; 568/804
[58] Field of Search .............. 568/804, 716, 744; 252/397

[56] References Cited

U.S. PATENT DOCUMENTS 4,105,698  8/1978  Starks et al. ............... 568/744
4,105,699  8/1978  Starks ......................... 568/744

OTHER PUBLICATIONS

Huston et al., Chem. Soc. 53, pp. 2379–2382, Jun. 1931.

Primary Examiner—Werren B. Lone
Attorney, Agent, or Firm—Donald L. Johnson; John F. Sieberth; John F. Hunt

[57] ABSTRACT

Phenols having an unsubstituted ortho-position are benzylated by reaction with a benzyl alcohol in contact with an activated alumina catalyst especially gamma alumina at a temperature sufficient to maintain the reactants in the vapor phase.

11 Claims, No Drawings

CHEMICAL PROCESS FOR PREPARING DI-ORTHO BENZYL PHENOLS

BACKGROUND

Ortho-alkylated phenols are valuable as antioxidants and chemical intermediates. One method of making them is by the reaction of an olefin with a phenol in the presence of an aluminum phenoxide catalyst (U.S. Pat. No. 3,831,898). Phenols have also been alkylated by reaction with an olefin using an alumina catalyst (U.S. Pat. No. 3,367,981). L. H. Klemm et al report the ortho-alkylation of phenol with n-propanol using an alumina catalyst (J. Org. Chem. 45, pages 4320–6).

Much less seems to be known about the benzylation of phenols. W. J. Hickenbottom, J. Chem. Soc., 80, pages 2844–9, report the preparation of 2-benzyl, 2,4-dibenzyl and 2,6-dibenzyl phenols by heating phenol with sodium hydroxide in toluene and reacting this with benzyl chloride.

R. C. Huston et al, J. Am. Chem. Soc. 53, page 2379, describe the reaction of benzyl alcohol with p-cresol using an aluminum chloride catalyst to make dibenzyl-p-cresol.

Brindell et al U.S. Pat. No. 3,816,544 disclose the reaction of 2,6-di-benzylphenol with formaldehyde to form 4,4'-methylenebis-(2,6-di-benzylphenol) but do not disclose any process for making 2,6-dibenzyl phenol.

The most pertinent reference relative to the present invention is believed to be Starks U.S. Pat. No. 4,105,688, which discloses the reaction of phenol and benzyl alcohol in the liquid phase using an α-alumina monohydrate catalyst to make mainly ortho-benzyl phenol plus minor amounts of 2,6-dibenzyl phenol.

SUMMARY

According to the present invention, o-benzylated phenols are made in high yield in a continuous process by passing a mixture of a phenol and a benzyl alcohol in the vapor phase through an activated alumina catalyst at about 225°–450° C.

DESCRIPTION OF PREFERRED EMBODIMENTS

A preferred embodiment of the invention is a process for making benzyl substituted phenols, said process comprising contacting a mixture of a phenol and a benzyl alcohol in the vapor phase with an activated alumina catalyst at a temperature in the range of 225°–450° C., said temperature being high enough to maintain said phenol and benzyl alcohol in the vapor phase at reaction conditions, said phenol having at least one position ortho or para to its phenolic hydroxyl group unsubstituted except for hydrogen.

The process is applicable to a broad range of phenols. The term "a phenol" is used in a generic sense to include all aromatic hydroxy compounds having at least one hydroxy group bonded to an aromatic ring. The phenol must be capable of being heated to a temperature high enough to convert it to the vapor phase without excessive decomposition. Examples of typical phenols include phenol, o-cresol, p-cresol, 4-ethyl phenol, 4-phenyl phenol, α-naphthol, β-naphthol, 4-chlorophenol, 1-chlorophenol, 2,4-dichlorophenol, 4-bromophenol, hydroquinone, 4-methoxy phenol, 4-ethoxy phenol, and the like.

A preferred class of phenols contains the structure

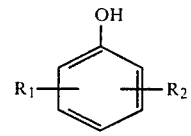

wherein $R_1$ and $R_2$ are selected from the group consisting of hydrogen alkyl containing 1–20 carbon atoms, alkenyl containing 2–20 carbon atoms, cycloalkyl containing 5–8 carbon atoms, aryl containing 6–12 carbon atoms, halogen, hydroxy, and $C_{1-4}$ alkoxy.

These include 2,4-dimethyl phenol, 4-n-octyl phenol, 4-sec-eicosyl phenol, 4-allyl phenol, 4-stearyl phenol, 4-cyclohexyl phenol, 2-cyclopentylphenol, 4-(2,4-dimethylphenyl)phenol, 2-bromophenol, 2,4-dibromophenol, 4-chlorophenol, 4-methoxyphenol, 4-ethoxyphenol, 4-propoxyphenol, 4-butoxyphenol, 4-isobutoxyphenol, hydroquinone, and the like.

Highly preferred reactants are the compound phenol, $C_6H_5OH$, and mono lower alkyl derivatives thereof such as p-cresol, o-cresol, p-ethylphenol, p-n-butylphenol, and the like. The most preferred phenol reactant is the compound phenol.

Benzyl alcohols are the class of compounds which have a hydroxy methyl group bonded to a benzene ring. The benzene ring may be unsubstituted or may be substituted with groups such as alkyl, halogen, alkoxy, and the like. Typical benzyl alcohols include p-methylbenzyl alcohol, p-ethylbenzyl alcohol, o-methylbenzyl alcohol, p-isobutylbenzyl alcohol, p-chlorobenzyl alcohol, 2,4-dichlorobenzyl alcohol, o-bromobenzyl alcohol, p-methoxybenzyl alcohol, p-ethoxybenzyl alcohol, and the like. The most preferred benzylating agent is the compound benzyl alcohol, $C_6H_5CH_2OH$.

The phenol reactant and benzyl alcohol reactant may be used in a wide mole ratio range such as 0.2–10 moles of the benzyl alcohol per mole of the particular phenol. It has been found that it is not beneficial to use much excess benzyl alcohol because it tends to react with itself to form dibenzyl ethers.

A more preferred reactant ratio when di-benzylation is desired is about 1–3 moles of the benzyl alcohol reactant per mole of the phenolic reactant. When reacting the compound benzyl alcohol with the compound phenol, it has been found that high yields of 2,6-dibenzyl phenol require a ratio of about 1.5–2.5 moles of benzyl alcohol per mole of phenol.

When mono-benzylation is desired, the amount of benzyl alcohol reactant should be reduced to about 0.2–1.5 moles, more preferably 0.5–1.0 moles per mole of phenolic reactant.

Although a broad range of activated aluminas may be used, they are not all equivalent in performance. Representative activated aluminas include gamma, delta, eta, theta, kappa, chi and rho (Alumina Properties, Russel et al, published by Aluminum Company of America, 1956).

The most preferred alumina is gamma-alumina. This alumina gives exceptionally high yields in the vapor phase reaction and exhibits an extremely low deactivation rate.

The process is carried out by placing an alumina catalyst bed in a suitable container and heating the catalyst bed to the desired temperature. This temperature should be high enough to maintain both the phenolic reactant and benzyl alcohol reactant in the vapor phase under the particular conditions such as pressure. The reaction is preferably conducted at close to atmospheric pressure although higher and lower pressures may be used. The temperature should also be high enough to cause the benzylation to proceed at a reasonable rate, but not so high as to cause decomposition. A useful range in which to experiment is about 225°–450° C. Very good results have been achieved in the case of the compounds phenol and benzyl alcohol at temperatures of about 250°–450° C.

While the catalyst bed is being heated to reaction temperature, it can be purged with an inert gas such as nitrogen. This will prevent oxidation of the reactants once chemical feed is started.

The phenolic and benzyl alcohol can be fed to the heated catalyst in separate feeds. An easy way to control the mole ratio is to first mix the phenolic reactant and benzyl alcohol reactant in the desired mole ratio and then feed the mixture to the heated catalyst. The mixture is preferably heated such that it provides a liquid feed.

The liquid feed can be fed directly to the catalyst bed. Preferably, the liquid feed is first passed through a preheater which rapidly heats the liquid feed to form a vapor mixture. The vapor is then passed through the catalyst bed.

Only a short contact time of the vapor mixture with the catalyst is required. Contact times of one second to about 10 minutes are effective. A more preferred contact time is about 5 seconds to 5 minutes. A still more preferred contact time is about 5 seconds to one minute.

After traversing the catalyst bed, the effluent product is cooled to condense all vapors. After the water formed in the reaction is removed, the crude product may then be distilled to recover the desired product(s) and unconverted starting material.

The following example shows how the process has been carried out.

EXAMPLE 1

A continuous catalytic reactor was made by placing a pelleted gamma alumina (Harshaw 3438 T gamma alumina) in a quartz tube about 30 cm. length and 2.5 cm. in diameter. The 5 cm. catalyst plug (approximately 16 g.) was held in place between 5 cm. of glass beads at the bottom of the tube and glass beads above the catalyst up to the top of the tube. Temperature in the catalyst was measured using a thermocouple probe. The top glass bead section functions as a pre-heater and had a separate electrical heater. The top of the tube was fitted with a nitrogen inlet and a dropping funnel. The bottom connected through an air cooled condenser to a glass receiver.

In the initial run the catalyst bed was heated to 330°–340° C. while purging the system with nitrogen. Then a 6:1 mole ratio mixture of benzyl alcohol and phenol was fed dropwise at the top of the tube at about 0.2 ml. per minute. This was vaporized in the pre-heater section and the vapors passed downward through the gamma alumina catalyst. The products passed through the air cooled condenser and were collected in the receiver.

The major components in the effluent by VPC analysis were:

|  | Percent |
|---|---|
| 2,6-dibenzyl phenol | 18.9 |
| 2,4,6-tribenzyl phenol | 6.8 |
| benzyl alcohol | 25.2 |
| dibenzyl ether | 15.2 |
| benzaldehyde | 11.4 |
| light unknown | 16.8 |

EXAMPLES 2–6

These examples were conducted in the same manner as Example 1 except for reactant ratio and temperature. The following table gives the reaction conditions:

| Example | Temperature °C. | Benzyl Alcohol to Phenol Mole Ratio | Feed Time (hrs.) | Total Feed (g.) |
|---|---|---|---|---|
| 2 | 275–340 | 6:1 | 1.25 | 42 |
| 3 | 290–300 | 6:1 | 5 | 84 |
| 4 | 290–300 | 3:1 | 3 | 87 |
| 5 | 300–320 | 2.5:1 | 6 | 136 |
| 6 | 280–290 | 2:1 | 33 | 585 |

| Product | Example 2[1] | 3[2] | 4[2] | 5[2] | 6[2] |
|---|---|---|---|---|---|
| o-monobenzyl phenol | 0.7–1.4 | 0.6–1.3 | 1–3.2 | 0.4–1 | 6.2–3.8 |
| 2,6-dibenzyl phenol | 18.9–13.0 | 12–14.4 | 49–41 | 67.7–66.9 | 75–77 |
| tribenzyl phenol | 6.8–7.3 | 5.4–8.0 | 16.3–13 | 18.9–19.3 | 11–14 |
| benzyl alcohol | 25.2–48.1 | 32.7–41.2 | 11.7–19.9 | 2.1–2.2 |  |
| dibenzyl ether | 15.2–16.3 | 29–17.3 | 6.8–5.5 | 0.6–0.6 |  |
| light unknown[3] | 16.8–2.8 | 7.8–5 | 7.7–2 | 0.2–2.4 |  |

[1] The first value is at the first stage of the reaction at 330–340° C. and the second value is at the final stage of the reaction at 275–285° C.
[2] The first value is at the start of the process and the second is towards the end
[3] Probably toluene These results show the critical sensitivity of dibenzyl phenol yield on the benzyl alcohol-phenol mole ratio. At 6:1, less than 20 percent of the effluent was the desired dibenzylphenol. At 3:1, almost half of the product was dibenzylphenol and at 2:1, three-quarters of the effluent was dibenzylphenol.

EXAMPLES 7–8

Two more experiments were conducted at still lower mole ratios. Both were conducted at 280°–290° C. using 16 g. Harshaw H-3438 T gamma alumina.

| Example | Mole Ratio | Total Time | Total Feed | Percent Benzylphenol | | |
|---|---|---|---|---|---|---|
|  |  |  |  | o-Mono | 2,6-Di | Tri |
| 7 | 1.75:1 | 7 hr. | 88 g. | 4.5–8 | 68–73.7 | 20–11 |
| 8 | 1.5:1 | 10.5 hr. | 97 g. | 8.2–13 | 74.5–64 | 11–10.9 |

EXAMPLE 9

This experiment was conducted to measure the decay rate of catalytic activity. The same Harshaw H-3438T gamma alumina catalyst (16 g.) was used. The reaction zone was maintained at about 280°–290° C. Over a 33 hour period, 2.7 Kg of a 2:1 mole mixture of benzyl alcohol:phenol was passed through the catalyst in the vapor phase. Feed rate was varied during the course of the reaction to determine the effect of contact time on conversion. The composition of the product was as follows (VPC):

|  | Initial | Mid-point | End |
|---|---|---|---|
| Phenol | 2.6 | 4.1 | 4.3 |
| Benzyl alcohol | — | 3.3 | 4.6 |
| 2-Benzylphenol | 6.6 | 6.0 | 6.5 |
| 2,6-Dibenzylphenol | 72.3 | 64.6 | 66.2 |
| 2,4,6-Tribenzylphenol | 13.9 | 16.0 | 11.7 |

The highest conversion to 2,6-dibenzylphenol was at a feed rate of 16 g. hr. (76 percent) although even at a much higher feed rate of 56 g. hr. the product was 65.1 percent 2,6-dibenzylphenol. From this it can be seen that the process is capable of very high production rates.

An experiment was carried out by reacting benzyl alcohol with phenol in the liquid phase using a gamma alumina catalyst for comparative purposes.

COMPARATIVE EXAMPLE 10

In a reaction vessel was placed 47 g (0.5 mole) phenol, 75.6 g (1.2 moles) benzyl alcohol and 7.5 g. powdered gamma alumina (Harshaw 3438). The vessel was fitted with a stirrer and a Dean Stark water trap. Over a four hour period the mixture was heated to 180° C. It was then stirred at 180°–190° C. for three hours. Sample 1 was taken at two hours and Sample 2 at three hours. The mixture was stirred at 180°–190° C. for five more hours and then Sample 3 was taken. Following are the results:

| Sample | Reaction Time | Product Composition (area percent) 2-benzylphenol | 2,6-dibenzylphenol |
|---|---|---|---|
| 1 | 2 hrs. | 21.3 | 8.6 |
| 2 | 3 hrs. | 25.0 | 25.7 |
| 3 | 8 hrs. | 42.3 | 52.9 |

The results show that the reaction is very slow in the liquid phase. Only 52.9 area percent (by Gas Chromatograph) 2,6-dibenzylphenyl had formed after 8 hours reaction.

The compounds made by the present process are useful in providing antioxidant protection in a broad range of organic materials of the type normally subject to oxidative deterioration in the presence of oxygen during use over an extended period. In other words, the organic compositions protected by the present antioxidants are the type in which the art recognizes the need for antioxidant protection and to which an antioxidant of some type is customarily added to obtain an extended service life. The oxidative degradation protected against is the slow gradual deterioration of the organic composition rather than, for example, combustion. In other words, the present additives are not flame retarding additives nor flame suppressing additives and the degradation protected against is not combustion, but rather the gradual deterioration of the organic composition due to the effects of oxygen over an extended period of time.

The preferred antioxidants are 2,6-dibenzylphenol and 2,6-dibenzyl-4-alkylphenol wherein the alkyl group contains 1–20 carbon atoms.
These include:
2,6-dibenzyl-4-methylphenol
2,6-dibenzyl-4-ethylphenol
2,6-dibenzyl-4-n-propylphenol
2,6-dibenzyl-4-n-butylphenol
2,6-dibenzyl-4-sec-butylphenol
2,6-dibenzyl-4-n-dodecylphenol
2,6-dibenzyl-4-(1-methylnonadecylphenol)
2,6-dibenzyl-4-(2-ethylhexyl)phenol, and the like.

Examples of organic materials in which the additives are useful include polyolefins such as polyethylene, polypropylene, polybutadiene, and the like. Copolymers of olefinically unsaturated monomers such as styrene-butadiene rubber (SBR rubber), ethylene-propylene-diene terpolymers such as the terpolymer of ethylene, propylene and cyclopentadiene or cyclooctadiene, likewise, acrylonitrile butadiene-styrene resins are effectively stabilized. Ethylene-vinyl acetate copolymers are protected, as are butene methylacrylate copolymers. Nitrogen-containing polymers such as polyurethanes, nitrile rubber, and lauryl acrylate-vinylpyrolidone copolymers are effectively stabilized. Adhesive compositions such as solutions of polychloroprene (neoprene) in toluene are protected. Fats and oils of animal and vegetable origin are protected against gradual deterioration. Examples of these are lard, beef tallow, coconut oil, safflower oil, castor oil, babassu oil, cottonseed oil, corn oil, rapeseed oil, and the like.

Petroleum oils and waxes such as solvent-refined, midcontinent lubricating oils are effectively stabilized. Animal feeds such as ground corn, cracked wheat, oats, wheat germ, alfalfa, and the like, are protected by mixing a small but effective amount of the present additive with these products. Vitamin extracts, especially the fat-soluble vitamins such as Vitamin A, B, D and C, are effectively stabilized against degradation. The additives are useful in foamed plastics such as expanded polystyrene, polyurethane foams, and the various foamed rubbers, alkyd resins such as short oil terephthalic acid-glycerol-linseed oil resins, and typical long oil resins of trimellitic acid-glycol-tung oil resins including epoxide-modified alkyl resins. Epoxy resins themselves such as isopropylidenebisphenol-epichlorohydrin epoxy resins are stabilized against degradation.

Hydrocarbons such as gasoline, kerosene, diesel fuel, fuel oil, furnace oil, and jet fuel are effectively protected. Likewise, synthetic hydrocarbon lubricants, for example, α-decene trimer, polybutene lubricants, di- and tri-$C_{12-30}$ alkylated benzene and naphthalene synthetic lubricants are likewise protected.

Organometallics such as tetraethyllead, tetramethyllead, tetravinyllead, ferrocene, methyl ferrocene, cyclopentadienyl manganese tricarbonyl, methyl cyclopentadienyl manganese tricarbonyl, cyclopentadienyl nickel nitrosyl, and the like, are effectively protected against oxidative degradation. Silicone oils and greases are also protected.

Synthetic ester lubricants such as those used in turbines and turbojet engines are given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethyleneglycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates, and poly-6-aminohexanoic acid (nylon) are effectively stabilized. Polyalkylene oxides such as copolymers of phenol with ethylene oxide or propylene oxide are stabilized. Polyphenyl ethers such as poly-2,6-dimethylphenyl ether formed by polymerization of 2,6-dimethylphenol using a copper-pyridine catalyst are stabilized. Polycarbonate plastics and other polyformaldehydes are also protected.

Linear poly esters such as phthalic anhydride-glycol condensates are given a high degree of protection. Other poly esters such as trimellitic acid-glycerol condensates are also protected. Polyacrylates such as polymethylacrylate and polymethylmethacrylate are effectively stabilized. Polyacrylonitriles and copolymers of acylonitriles with other olefinically unsaturated monomers such as methylmethacrylates are also effectively stabilized.

The additives can be used to protect any of the many organic substrates to which an antioxidant is normally added. It can be used where economics permit to protect such substrates as road tar, paper, polyvinyl acetate, coumarone-indene resins, polyvinyl esters, polyvinylidene bromide, acrylonitrile, vinyl bromide copolymer, vinyl butyral resins, silicones such as dimethylsilicone lubricants, phosphate lubricants such as tricresylphosphate, and the like.

The additives are incorporated into the organic substrate in a small but effective amount so as to provide the required antioxidant protection. A useful range is from about 0.01 to about 5 weight percent, and a preferred range is from about 0.1 to 3 weight percent.

The additives can be used alone or together with a synergist. Exceptionally effective synergists, especially in homopolymers and copolymers of ethylenically unsaturated monomers, are the di-$C_{4-30}$ alkyl thiodipropionates such as dilauryl thiodipropionate and distearyl thiodipropionate. A useful range for such synergists is about 0.01–5 weight percent and a more preferred range is 0.1–3 weight percent.

Methods of incorporating the additive into the substrate are well known. For example, if the substrate is liquid the additive can be merely mixed into the substrate. Frequently, the organic substrate is in solution and the additive is added to the solution and the solvent removed. Solid organic substrates can be merely sprayed with a solution of the additive in a volatile solvent. For example, stabilized grain products result from spraying the grain with a toluene solution of the additive. In the case of rubbery polymers the additive can be added following the polymerization stage by mixing it with the final emulsion or solution polymerization mixture and then coagulating or removing solvent to recover the stabilized polymer. It can also be added at the compounding stage by merely mixing equipment such as a Banbury blender. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized. The following will serve to illustrate the manner in which the additives are blended with various organic substrates.

EXAMPLE 11

To a synthetic rubber master batch comprising 100 parts of SBR rubber having an average molecular weight of 60,000, 50 parts of mixed zinc propionate stearate, 50 parts carbon black, 5 parts road tar, 2 parts sulfur and 1.5 parts of mercapto benzothiazole is added 1.5 parts of 2,6-dibenzyl-p-cresol. After mastication, the resultant master batch is cured for 60 minutes using 45 psi steam pressure, resulting in a stabilized SBR vulcanizate.

EXAMPLE 12

A synthetic SBR polymer is prepared by polymerizing 60 percent styrene and 40 percent butadiene in an aqueous emulsion employing a sodium oleate emulsifier and a peroxide catalyst. Following this, sufficient 2,6-dibenzyl phenol is added to provide 0.3 weight percent, based upon the SBR polymer. The emulsion is then coagulated using an acidified salt solution and the coagulated polymer compressed into bales for storage. The polymer is quite stable during storage and can later be compounded to prepare SBR vulcanizates.

EXAMPLE 13

A cis-polybutadiene polymer is prepared having 90 percent cis configuration by polymerizing butadiene in a toluene solvent employing a diethyl aluminum chloride-cobalt iodide catalyst. Following the polymerization, a small amount sufficient to provide 0.2 weight percent of 2,6-dibenzyl-4-ethylphenol is added to the toluene solution, following which the solution is injected into boiling water together with steam causing the solvent to distill out and the cis-polybutadiene to coagulate, forming a rubber crumb. The crumb is dried and compressed into bales, resulting in a stabilized cis-polybutadiene.

EXAMPLE 14

A butadiene-acrylonitrile copolymer is prepared from 1,3-butadiene and 32 percent of acrylonitrile. One percent based on the weight of polymer, 2,6-dibenzyl-4-methoxyphenol is added as an emulsion in a sodium oleate solution. The latex is coagulated and the coagulum is washed and dried, resulting in a stabilized butadiene-acrylonitrile copolymer.

EXAMPLE 15

To 1000 parts of a solid polypropylene powder is added 5 parts of 2,6-dibenzyl-4-methylphenol and 10 parts of dilaurylthiodipropionate. The mixture is heated to its melting point and rapidly stirred and extruded to form a useful polypropylene filament.

EXAMPLE 16

To 1000 parts of polyethylene is added 3 parts of 2-benzyl-4,6-dimethylphenol and 5 parts of dilaurylthiodipropionate. The mixture is heated to its melting point and stirred and then passed through an extruder having a central mandrel to form tubular polyethylene which is inflated to form a useful polyethylene film.

EXAMPLE 17

To 100,000 parts of a midcontinent, solvent-refined, mineral oil having a viscosity of 100° F. of 373.8 SUS and at 210° F. of 58.4 SUS is added 500 parts of 2,6-dibenzyl phenol. Following this, is added 100 parts of a zinc dialkyldithiophosphate, 50 parts of an overbased calcium alkaryl sulfonate, 1000 parts of a poly dodecylmethacrylate VI improver and 2000 parts of a 70 percent active oil solution of an alkenyl succinimide of tetraethylenepentamine in which the alkenyl group has a molecular weight of 950. The resultant mixture is blended while warm, following which it is filtered and packaged, giving a stable lubricating oil useful in automotive engines.

EXAMPLE 18

To 10,000 parts of a dimethyl silicone lubricating oil is added 50 parts of 2,6-dibenzyl-4-n-butyl-phenol. The mixture is stirred at 50° C. until thoroughly blended, resulting in a stable silicone lubricating oil.

EXAMPLE 19

To 10,000 parts of corn oil is added 15 parts of 2,6-dibenzyl-4-methyl phenol. The mixture is stirred, giving a corn oil highly resistant to normal oxidative degradation.

EXAMPLE 20

To 10,000 parts of trimethylolpropane tripelargonate is added 200 parts of tricresylphosphate, 10 parts of dimethyl silicone, 10 parts of benzothiazole, 50 parts of phenyl-β-naphthol amine, and 50 parts of 2-benzyl-6-isopropyl phenol resulting in a stabilized synthetic ester lubricant.

EXAMPLE 21

Wax paper is made by impregnating paper with paraffin wax containing 0.05 weight percent of 2,6-dibenzyl-4-n-propyl phenol. The wax paper is used to make containers for potato chips which results in chips having extended shelf life.

EXAMPLE 22

To 10,000 parts of gasoline having an 87 R.O.N. is added 20 parts of 2,6-dibenzyl phenol and sufficient commercial tetraethyllead antiknock fluid to provide 2.5 grams of lead per gallon, resulting in a stabilized gasoline having a 96 R.O.N.

EXAMPLE 23

To 10,000 parts of 41 cetane diesel fuel is added 50 parts of hexyl nitrate and 25 parts of 2,6-dibenzyl phenol providing a stable diesel fuel.

EXAMPLE 24

To 10,000 parts of melted lard is added 10 parts of 2,6-dibenzyl-p-cresol and the mixture is stirred until thoroughly blended, resulting in a lard highly resistant to normal oxidative degradation.

From the foregoing, it should be apparent how to prepare stable organic compositions using the additives of this invention.

Tests were carried out which demonstrate the antioxidant effectiveness of the additives of this invention. In one test the antioxidant properties of the compound in lubricating oil were measured. In this test an oil sample was prepared containing 0.005 wt. percent of Fe or tin naphthenate as an oxidation catalyst. A clean copper-lead bearing was also placed in the oil. The test additive was also dissolved in the oil. This oil was heated to 160° C. and air was bubbled through this oil at a rate of 0.2 l/min. for 18 hours. After this period the viscosity of this oil was measured and compared to the original viscosity. An increase in viscosity is a measure of the degree of oxidative degradation.

| Additive | Conc. (wt. %) | % Visc. Increase |
| --- | --- | --- |
| None | — | 957 |
| 2,6-dibenzylphenol | 1.0 | 112 |

The additive was quite effective in controlling the amount of viscosity increase caused by oxidation.

In another test, the antioxidant effectiveness of the products in polypropylene was measured. Test polypropylene specimens were prepared which were 25 mils thick and contained various amounts of test additive. Five replicates of each concentration were made. The specimens were placed in an air circulating oven at 150° C. and observed daily. Each test terminated when three of the five specimens failed as shown by cracking or other visual evidence. Hours to failure was used as the test criteria.

| | Additive | Conc (wt. %) | Hours to Failure |
| --- | --- | --- | --- |
| 1. | None | — | 3–4 |
| 2. | 2,6-dibenzylphenol | 0.1 | 24 |
| 3. | 2,6-dibenzylphenol plus synergist[1] | 0.1 0.25 | 364 |
| 4. | 2,6-dibenzyl-p-cresol | 0.1 | 24 |
| 5. | 2,6-dibenzyl-p-cresol plus synergist[1] | 0.1 0.25 | 412 |

[1]distearylthiodipropionate

The additive are seen to have antioxidant effectiveness which is greatly enhanced by synergists.

The compounds have other uses. For example, 2-benzyl-4-chlorophenol is a very effective disinfectant.

We claim:

1. A process for making benzyl substituted phenols, said process comprising contacting a mixture of a phenol and a benzyl alcohol in the vapor phase with an activated gamma alumina catalyst at a temperature in the range of 225°–450° C., said temperature being high enough to maintain said phenol and benzyl alcohol in the vapor phase at reaction conditions, said phenol having at least one position ortho or para to its phenolic hydroxyl group unsubstituted except for hydrogen.

2. A process of claim 1 wherein the mole ratio of said benzyl alcohol to said phenol is about 1–3:1.

3. A process of claim 2 wherein said temperature is about 250°–350° C.

4. A process of claim 1 wherein said phenol has the structure

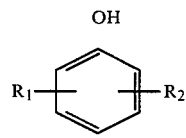

wherein $R_1$ and $R_2$ are selected from the group consisting of hydrogen, alkyl containing 1–20 carbon atoms, alkenyl containing 2–20 carbon atoms, cycloalkyl containing 5–8 carbon atoms, aryl containing 6–12 carbon atoms, halogen, hydroxy and $C_{1-4}$ alkoxy.

5. A process for selectively di-orthobenzylating a phenol which is unsubstituted except for hydrogen in both positions ortho to its phenolic hydroxyl group, said process comprising contacting a mixture of said phenol and said benzyl alcohol in the mole ratio of about 1:1–3 in the vapor phase with a gamma-alumina catalyst at a temperature in the range of about 225°–450° C., said temperature being high enough to maintain said phenol and benzyl alcohol in the vapor phase under reaction conditions.

6. A process of claim 5 wherein said phenol is the compound phenol and further comprising the step of recovering therefrom as the major product 2,6-dibenzylphenol.

7. A process of claim 6 wherein the mole ratio of said benzyl alcohol to said phenol is about 1–3:1 and said temperature range is about 250°–350° C.

8. A process of claim 7 wherein said mole ratio is about 1.5–2.5:1.

9. Organic material normally susceptible to gradual degradation due to the effects of oxygen containing an antioxidant amount of a compound selected from the group consisting of 2,6-dibenzyl phenol and 2,6-dibenzyl-4-alkyl phenol wherein said alkyl contains about 1–12 carbon atoms.

10. An organic composition of claim 9 wherein said compound is a 2,6-dibenzyl-4-alkylphenol.

11. An organic composition of claim 10 wherein said compound is 2,6-dibenzyl-4-methylphenol.

* * * * *

UNITED STATES PATENT AND TRADEMARK OFFICE
CERTIFICATE OF CORRECTION

PATENT NO. : 4,514,577
DATED : APRIL 30, 1985
INVENTOR(S) : ALLEN H. FILBEY, ET AL.

It is certified that error appears in the above-identified patent and that said Letters Patent is hereby corrected as shown below:

Column 3, line 53, reads "electrical heater. The top of the . . ." and a sentence should appear after "heater." reading -- The catalyst section was heated by a separate clam-shell type electric heater. --.

Column 5, line 43, reads "2,6-dibenzylphenyl" and should read -- 2,6-dibenzylphenol --.

Signed and Sealed this

Twentieth Day of August 1985

[SEAL]

Attest:

DONALD J. QUIGG

Attesting Officer      Acting Commissioner of Patents and Trademarks